United States Patent [19]

Schneider et al.

[11] Patent Number: 5,569,760
[45] Date of Patent: Oct. 29, 1996

[54] PROCESS FOR PREPARING NEVIRAPINE

[75] Inventors: Heinrich Schneider; Albrecht Christmann, both of Ingelheim am Rhein, Germany

[73] Assignee: Boehringer Ingelheim KG, Ingelheim am Rhein, Germany

[21] Appl. No.: 371,622

[22] Filed: Jan. 12, 1995

[30] Foreign Application Priority Data

Feb. 3, 1994 [DE] Germany ............... 44 03 311.7

[51] Int. Cl.$^6$ .................................................. C07D 471/14
[52] U.S. Cl. ........................................................ 540/495
[58] Field of Search ............................................ 540/495

[56] References Cited

U.S. PATENT DOCUMENTS 5,366,972  11/1994  Hargrave ................... 514/220

FOREIGN PATENT DOCUMENTS 0429987  6/1991  European Pat. Off. .

OTHER PUBLICATIONS

Saunders, Drug Design and Discovery, 8, 255–263 (1992).
Karl D. Hargrave et al., *J. Med. Chem.* 34, 2231–2231 (1991).
M. H. Norman et al., *J. Heterocyclic Chem.*, 30, 771–779 (1993).
Haslir et al., J. Infect Diseases 171, 537 (1995).
Wei, Nature 373, 117 (1995).
O'Brien, New. Eng. J. Medicine 334, 426 (1996).

*Primary Examiner*—Mark L. Berch
*Attorney, Agent, or Firm*—R. P. Raymond; A. R. Stempel; W. E. Rieder

[57] ABSTRACT

A process for preparing nevirapine which comprises reacting 2-chloro-N-(2-chloro-4-methyl-3-pyridyl)-3-pyridine carboxamide with cyclopropylamine followed by cyclisation of the product, wherein the reaction with cyclopropylamine is carried out in the presence of an oxide or hydroxide of an element of the second main or sub-group of the periodic table of elements.

7 Claims, No Drawings

PROCESS FOR PREPARING NEVIRAPINE

The present invention relates to an improved process for preparing nevirapine, a non-nucleoside inhibitor of HIV-1 reverse transcriptase which is useful for the treatment of HIV-1 infection in humans. The structural formula for nevirapine, 11-cyclopropyl- 5,11-dihydro-4-methyl-6-H-dipyrido[3,2-b:2',3'-e][1,4]diazepin-6-one, is:

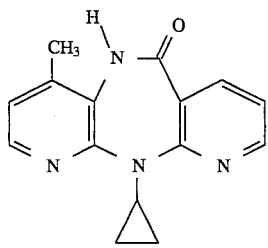

A process for preparing nevirapine, in which 2-chloro-3-pyridine carbonyl chloride (2) is reacted with 3-amino-2-chloro-4-methylpyridine (3), is known from the prior art [K. D. Hargrave et al., *J. Med Chem.* 34, 2231 (1991); M. H. Norman, D. J. Minick and G. E. Martin, *J. Heterocyclic Chem.* 30, 771 (1993); and U.S. Pat. No. 5,366,972]. This prior art process is depicted in the following reaction scheme.

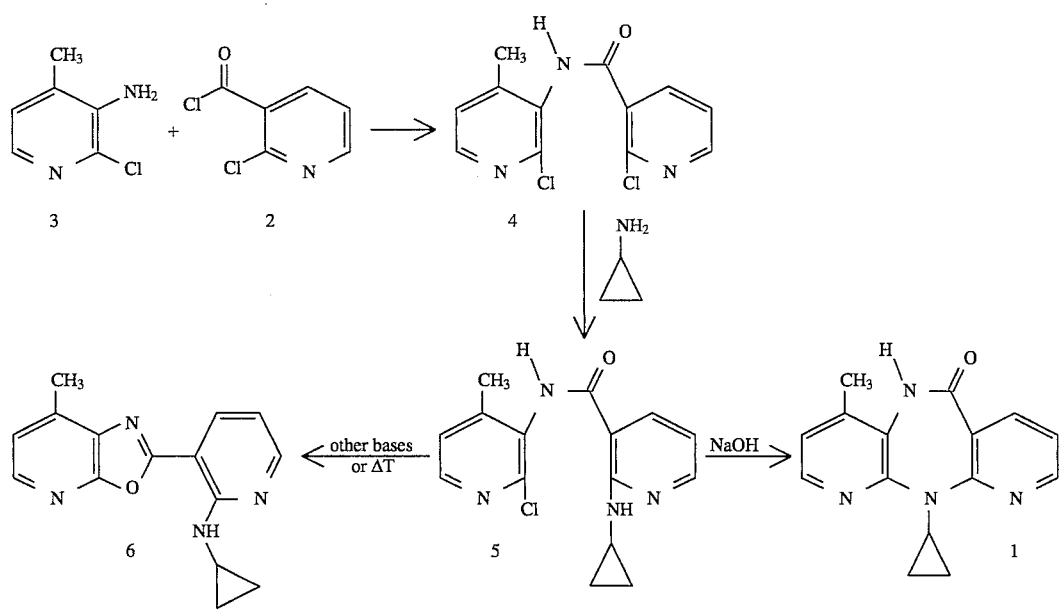

The acylation agent (2) is formed by reacting 2-chloro-3-pyridine-carboxylic acid with thionyl chloride. The reaction of (2) with (3) produces 2-chloro-N-(2-chloro-4-methyl-3-pyridinyl)-3-pyridine carboxamide (4), which reacts with cyclopropylamine to give N-(2-chloro-4-methyl-3-pyridyl)-2-(cyclopropylamino)-3-pyridine carboxamide (5). The final step is the cyclisation to produce nevirapine (1) which occurs on treatment of (5) with sodium hydride.

The disadvantages of this prior art process are, inter alia, that a large excess of cyclopropylamine (about 400 mol-%) must be used for preparing N-(2-chloro-4-methyl-3-pyridyl)-2-(cyclopropylamino)-3-pyridine-carboxamides (5), and undesirable by-products, such as compound 6, are produced during this reaction.

Surprisingly, it has now been found that the large excess of the relatively expensive cyclopropylamine may be reduced if the reaction is carried out in the presence of an oxide or hydroxide of an element of the second main or second sub-group of the periodic table. Preferably an oxide or hydroxide of an alkaline earth metal or of zinc is used, with calcium oxide (CaO) being particularly preferred. By adding 0.5 to 2.5 mol of calcium oxide, the amount of cyclopropylamine used may be reduced to 2 to 2.5 mol of cyclopropylamine per mol of adduct 4 when converting 2-chloro-N-(2-chloro-4-methyl-3-pyridyl)-3-pyridine carboxamide (4) into N-(2-chloro-4-methyl-3-pyridyl)-2-(cyclopropylamino)-3-pyridine carboxamide (5). Furthermore, the reaction produces fewer impurities or side products. In addition, 10% less of the sodium hydride is required in the subsequent cyclisation step to produce nevirapine.

A further advantage of the process according to the invention is that the solvent may be recovered by distillation and used for a new reaction sequence. It has been found that when diglymes are used as the reaction solvent, the above distillate contains about 90 mol-% of cyclopropylamine which results in a saving of cyclopropylamine when the distillate is re-used as a solvent for the next preparation. The reaction may, moreover, be carried out on a large scale industrially without lowering the quality of the product.

There is a further technical advantage of the improved process in cases where the reaction can no longer be controlled as may, for example, be the case when the coolant is in short supply. The pressure in the reaction vessel may increase to 28–30 bar when 400 mol-% of cyclopropylamine are used, but it only increases to 8–9 bar when 250 mol-% are used. This means that apparatuses require a far lower pressure resistance than previously.

An additional advantage may be achieved if for the initial 30 minutes only 100–150 mol-% of cyclopropylamine are reacted and the remaining cyclopropylamine is then added. In this case, it may be possible to use stirring apparatuses according to DIN 28136 which are suitable for use at pressures up to 6 bar (Example 3).

The preparation of N-(2-chloro-4-methyl-3-pyridyl)-2-(cyclopropylamine)-3-pyridine carboxamides (5) and the subsequent cyclisation to produce 11-cyclopropyl-5,11-dihydro-4-methyl-6H-dipyrido-[3,2-b:2',3'-e][1,4]-diazepin-6-one (1) may, for example, be carried out on a large scale industrially as follows:

A mixture of 2-chloro-N-(2-chloro-4-methyl-3-pyridyl)-3-pyridine carboxamide (4), an oxide of an element of the second main or sub-group of the periodic table, preferably calcium oxide, and cyclopropylamine (100:100:250 mol-%) in an inert solvent, preferably diglyme (diethylene glycol-dimethylether) is heated to a temperature between 130° and 150° C., preferably 135° to 145° C., in an autoclave made of VA-steel over a period of 5 to 8 hours, preferably 6 to 7 hours.

The reaction mixture is then cooled to a temperature below 40° C., preferably to a temperature of 20° to 30° C., and filtered. The filter cake is washed with a suitable inert solvent such as dialkylether and, preferably, diglyme. The combined filtrates are concentrated and then diluted with an inert solvent, preferably diglyme. The resultant solution is added to a suspension or solution of a base, preferably a 60% suspension of sodium hydride in an inert solvent, preferably diglyme, at a temperature of 120° to 150° C., preferably 130° C. The reaction mixture is then stirred for a period of 0.5 to 1.5 hours, preferably 0.5 to 1.0 hours, at a temperature of 120° to 150° C., preferably 130° to 140° C. The reaction mixture and the volatile constituents of the reaction mixture are then distilled off as much as possible. The remaining residue is then carefully hydrolysed at a temperature of 20° to 90° C., preferably 50° to 80° C. After cooling to a temperature of about 25° C., the hydrolysed residue is mixed with an inert solvent, for example a hydrocarbon, preferably cyclohexane, and an organic acid, preferably glacial acetic acid, and stirred for a period of 0.5 to 1.5 hours, preferably one hour, at a temperature of 5° to 50° C., preferably of 10° to 25 ° C. The resultant suspension is then centrifuged and the centrifuged material is washed with an inert solvent such as dialkylether or a hydrocarbon, preferably methyl-tert.-butylether, and then with water and finally with an alcohol, preferably ethanol.

The following non-limiting examples illustrate the invention.

EXAMPLE 1

117.5 kg of 2-chloro-N-(2-chloro-4-methyl-3-pyridyl)-3-pyridine carboxamide (4), 23.3 kg of calcium oxide and 59.4 kg of cyclopropylamine (molar ratio: 1:1:2.5) are heated to between 135° and 145° C. in 235 l ofdiglyme (diethylene glycoldimethylether) in a 500 l VA autoclave over a period of 6 to 8 hours. The reaction mixture is then cooled to a temperature of 20° to 30° C. and filtered. The filter cake is washed with 58.8 l of diglyme. The filtrates are combined and initially 200 l of solvent is distilled off. The residue is then diluted with a further 117.5 l of diglyme. The resultant diluted solution is added over a period of 20 to 40 minutes to a suspension of 45.0 kg of 60% sodium hydride in 352.5 l of diglyme, heated to 130° C. The storage vessel and conduits are rinsed with a further 55.8 l of diglyme, and the mixture is stirred at a temperature of between 130° and 140° C. for a further 30 to 60 minutes. The majority of the diglyme is then distilled off. Finally, the remaining residue is carefully mixed with 470 l of water. After cooling to a temperature of about 25° C., 235.0 l of cyclohexane and 57.1 l of glacial acetic acid are added to the reaction mixture. The mixture is then stirred for about 1 hour at temperature of 10° to 25° C. The resultant suspension is centrifuged and the centrifuged material is then washed with 235.0 l of methyl-tert.-butylether and subsequently with 353.5 l of water and finally with 235 l of ethanol. In this way, after drying, 92.5 kg (83.5% of theory) of 11-cyclopropyl-5,11-dihydro-4-methyl-6H-dipyrido[ 3,2-b:2',3'-e][1,4]diazepin-6-one (nevirapine) is isolated.

EXAMPLE 2

117.5 kg of 2-chloro-N-(2-chloro-4-methyl-3-pyridyl)-3-pyridine carboxamide (4), 46.7 kg of calcium oxide and 47.5 kg of cyclopropylamine (molar ratio: 1:2:2) are heated to 135° to 145° C. in 235 l of diglyme (diethylene glycol dimethylether) in a 500 l VA autoclave over a period of 6 to 8 hours. The reaction mixture is then cooled to a temperature of 20° to 30° C. and filtered. The filter cake is washed with 58.8 l of diglyme. The filtrates are combined and about 188 l of solvent is distilled off. The residue is then diluted with a further 117.5 l of diglyme. Over a period of 20 to 40 minutes, the resultant diluted solution is added to a suspension of 45.0 kg of 60% sodium hydride in 352.5 l of diglyme, heated to 130° C. The storage vessel and conduits are rinsed with a further 55.8 l of diglyme and the mixture is stirred at a temperature of 130° to 140° C. for a further 30 to 60 minutes. The majority of the diglyme is then distilled off. Finally, the remaining residue is carefully mixed with 470.0 l of water. The reaction mixture is cooled to a temperature of about 25° C. and 235.0 l of cyclohexane and 57.1 l of glacial acetic acid are added. The mixture is then stirred for about 1 hour at a temperature of 10° to 25° C. The resultant suspension is centrifuged and the centrifuged material is washed with 235.0 l of methyl tert.-butylether, followed by 353.5 l of water and finally with 235 l of ethanol. In this way, after drying, 90.6 kg (81.7% of theory) of 11-cyclopropyl-5,11-dihydro-4-methyl-6H-dipyrido-[3,2-b:2',3'-e][1,4]diazepin-6-one (nevirapine) is isolated.

EXAMPLE 3

287.2 kg of 2-chloro-N-(2-chloro-4-methyl-3-pyridyl)-3-pyridine carboxamide (4), 57.0 kg of calcium oxide and 87.1 kg of cyclopropylamine (molar ratio: 1:1:1.5) are heated in 574 l of diglyme (diethylene glycol-dimethylether) to 135°–145° C. for about 30 minutes in a 1200 l VA stirring apparatus. This produces a pressure of 1.2–1.5 bar and about 50% of the starting material (4) is reacted. To this mixture, over about 30 minutes at 135°–145° C., a further 58.1 kg of cyclopropylamine is added producing a pressure of 3.0–3.5 bar, and another 25% of the starting material (4) is reacted. The mixture is then kept at 135°–145 ° C. for a period of 5 to 6 hours. The reaction mixture is then cooled to a temperature of 20° to 30° C. and filtered. The filter cake is washed with 144 l of diglyme. The filtrates are combined and 400 l of solvent is distilled off. The residue is then diluted with a further 287 l of diglyme. Over 20–40 minutes, the resultant diluted solution is added to a suspension of 110 kg of 60% sodium hydride in 862 l of diglyme, heated to 130° C. The storage vessel and conduits are rinsed with a further 144 l of diglyme and the mixture is stirred at a temperature of 130° to 140° C. for another 30 to 60 minutes. The majority of the diglyme is then distilled off. Finally, the remaining residue is carefully mixed with 1150 l of water. After the reaction mixture has been cooled to a temperature of about 25° C., 575 l of cyclohexane and 147 l of glacial acetic acid are added. The mixture is then stirred for about 1 hour at a temperature of 10°–25° C. The resultant suspension is centrifuged and the centrifuged material is then washed with 575 l of methyl-tert.-butylether, followed by 862 l of water and finally with 575 l of ethanol. In this way, after drying, 225 kg (83.0% of theory) of 11-cyclopropyl- 5,11-dihydro-4-methyl-6H-dipyrido[3,2-b :2',3'-e][1,4 ]diazepin-6-one (nevirapine) is obtained.

What is claimed is:

1. A process for preparing nevirapine which comprises reacting 2-chioro-N-(2-chloro-4-methyl-3-pyridyl)-3-pyridine carboxamide with cyclopropylamine followed by cyclisation of the product, wherein the reaction with cyclopropylamine is carried out in the presence of an oxide or hydroxide of an element of the second main or sub-group of the periodic table of elements.

2. The process according to claim 1, wherein the reaction of 2-chloro-N-(2-chloro-4-methyl-3-pyridyl)-3-pyridine carboxamide with cyclopropylamine is carried out in the presence of an oxide or hydroxide of an alkaline earth metal or of zinc.

3. The process according to claim 2, wherein the reaction of 2-chloro-N-(2-chloro-4-methyl-3-pyridyl)-3-pyridine carboxamide with cyclopropylamine is carried out in the presence of calcium oxide.

4. The process according to claim 3, wherein 2-chloro-N-(2-chloro-4-methyl-3-pyridyl)-3-pyridine carboxamide is heated with cyclopropylamine in the presence of 0.5 to 2 mol of calcium oxide in an inert solvent to a temperature of 130° to 150° C. over a period of 5 to 8 hours, the reaction mixture is then cooled to a temperature below 40° C. and filtered, the filter cake is washed with an inert solvent and the combined filtrates are concentrated, the residue is then diluted with an inert solvent and this solution is added to a solution or suspension of a base in an inert solvent, heated at 120° to 150° C., the reaction mixture is then kept at a temperature of 120° to 150° C. for 30 to 90 minutes, the reaction medium is then distilled off as much as possible and the residue is hydrolysed at a temperature of 20° to 90° C., the hydrolysed residue is cooled down and mixed with an inert solvent and an organic acid and the mixture is stirred at a temperature of 5° to 50° C. for 30 to 90 minutes, the product is then present as a suspension which is isolated and washed with an inert solvent, followed by water and an alcohol to give nevirapine.

5. The process according to claim 4, wherein 2-chloro-N-(2-chloro-4-methyl-3-pyridyl)-3-pyridine carboxamide is heated with cyclopropylamine in the presence of 1 to 2 mol of calcium oxide in diglyme to 135° to 145° C. for 6 to 7 hours, the reaction mixture is then cooled down to 20° to 30° C. and filtered, the filter cake is washed with diglyme and the combined filtrates are concentrated, the residue is then diluted with diglyme and this solution is added to a solution or suspension of sodium hydride in diglyme, heated to 130° to 140° C., and the reaction mixture is kept at a temperature of 130° to 140° C. for 30 minutes to one hour and then the reaction medium is distilled off, the residue is hydrolysed at a temperature of 50° to 80° C. and then cooled to a temperature of about 25° C. and mixed with an inert solvent and an organic acid and the reaction mixture is stirred for about 1 hour at 10° to 25° C., the resultant suspension of the product is separated, washed with an inert solvent, followed by water and alcohol to give nevirapine.

6. The process according to claims 1, 2, 3, 4 or 5, wherein initially only a portion of the cyclopropylamine is present and the remainder is added during the reaction.

7. The process according to claim 6, wheein, out of a total of 250 mol-% of cyclopropylamine used, only 100 to 150 mol-% are initially present.

* * * * *